United States Patent
Lin et al.

(10) Patent No.: US 7,181,979 B1
(45) Date of Patent: Feb. 27, 2007

(54) METHOD AND SYSTEM FOR INSPECTING FLEXIBLE DEVICE

(75) Inventors: Yan-Rung Lin, Pingtung County (TW); Shie-Chang Jeng, Pingtung County (TW); Chi-Chang Liao, Tainen (TW); Jyh-Wen Shiu, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 11/307,620

(22) Filed: Feb. 15, 2006

(30) Foreign Application Priority Data

Oct. 3, 2005 (TW) .............................. 94134467 A

(51) Int. Cl.
*G01N 3/20* (2006.01)
(52) U.S. Cl. ....................................................... 73/852
(58) Field of Classification Search ...................... None
See application file for complete search history.

(56) References Cited

U.S. PATENT DOCUMENTS

| | | | | |
|---|---|---|---|---|
| 3,388,591 A * | 6/1968 | Booth et al. .................. 73/800 |
| 4,640,583 A * | 2/1987 | Hoshikawa et al. ........ 349/153 |
| 4,708,020 A * | 11/1987 | Lau et al. ..................... 73/852 |
| 4,973,373 A | 11/1990 | Hashimoto et al. ......... 156/229 |
| 5,231,882 A * | 8/1993 | Bertele et al. ................ 73/852 |
| 6,067,860 A * | 5/2000 | Grams et al. ................. 73/814 |
| 6,437,846 B1 * | 8/2002 | Ono et al. .................... 349/149 |
| 7,026,758 B2 * | 4/2006 | Guenther et al. ........... 313/511 |
| 2002/0027634 A1 * | 3/2002 | Kang et al. ................. 349/150 |
| 2006/0137465 A1 * | 6/2006 | Lee et al. ..................... 73/794 |

* cited by examiner

*Primary Examiner*—Robert Raevis
(74) *Attorney, Agent, or Firm*—Jianq Chyun IP Office

(57) ABSTRACT

A system for inspecting a flexible device is provided, which is used for performing a performance inspection on a flexible device in a bending state, or after the flexible device has finished bending test so as to obtain a mechanical reliability. The inspecting system includes: at least one bending unit with at least one curvature; a conveyor unit used for conveying the flexible device so that a portion of the flexible device is passed through the bending unit and is bent into a bending portion; an inspecting unit performs a performance inspection on the flexible device. The performance inspection includes electrical, optical, or opto-electric inspection, and an inspection result can be recorded, displayed or both. The inspected flexible devices may be a flexible display device with complete or incomplete electrode thereon. In addition, a method for inspecting a flexible device is also provided.

14 Claims, 6 Drawing Sheets

METHOD AND SYSTEM FOR INSPECTING FLEXIBLE DEVICE

CROSS-REFERENCE TO RELATED APPLICATION

This application claims the priority benefit of Taiwan application serial no. 94134467, filed on Oct. 3, 2005. All disclosure of the Taiwan application is incorporated herein by reference.

BACKGROUND OF THE INVENTION

1. Field of Invention

The present invention relates to an inspecting technology for flexible devices. More particularly, the present invention relates to a system and method for inspecting a flexible device, which can perform at least a performance inspection on the flexible device in a bending state or a mechanical reliability inspection after the flexible device has finished bending test.

2. Description of Related Art

The trend of design and development of portable electronic products or consumptive electronic products is toward lightness, thinness and compactness. The flexible electronic product based on new plastic material is integrated with optical, electrical, and sensing functions. It can satisfy the ergonomics, wearability, flexibility and safety. And it is suitable for portable digital and multifunction electronic products. On the other hand, it has potential for the new application.

For example, a flexible display has the properties of thinness, lightness, impact resistance and flexibility, so it is rather portable. The products can be easily processed and cut into different shapes for diversified designs and provide considerable design freedom. It has a great potential to replace the conventional flat panel display as the next generation displays and to apply to a new marketplace. The special properties of a flexible display device also permit the transition from a sheet-fed batch processing to a roll-to-roll manufacturing. As a result, the production cost of the flexible display device will drop significantly.

A flexible electronic product or a flexible device may be used in a bending state or stored in a curved shape, and the optical, electrical, or opto-electric characteristic thereof may be affected or damaged. As to the flexible electronic product or flexible device, the performance inspection in bending state and after bending test is important during the research and development phase. In mass production, these characteristics also have to be inspected to ensure the quality of the products.

SUMMARY OF THE INVENTION

Accordingly, the present invention is to provide a method and system for inspecting a flexible device, which can perform a performance inspection on the flexible device when the flexible device is in a bending state.

The present invention provides a method and system for inspecting a flexible device, which can perform a performance inspection on the flexible device after the flexible device has finished bending test, to obtain a mechanical reliability.

The present invention provides a method for inspecting a flexible device, which includes: providing a flexible device to be inspected; providing at least one bending unit with at least one curvature; conveying the flexible device so that a portion of the flexible device is passing through the bending unit and is bent into a bending portion; and performing a performance inspection on the flexible device.

According to an embodiment of the present invention, in the inspecting method, the performance inspection is performed on at least one point of the bending portion.

According to an embodiment of the present invention, in the inspecting method, the performance inspection is performed on the flexible device after the flexible device has finished bending test, so as to obtain a mechanical reliability of the flexible device.

According to an embodiment of the present invention, in the inspecting method, the performance inspection includes electrical, optical, or opto-electric inspection, and an inspection result can be recorded, displayed or both.

According to an embodiment of the present invention, in the inspecting method, the flexible device can be a flexible display device without an attached electrode structure, and during the performance inspection, a required inspecting electric field is supplied to the flexible display device from external.

According to an embodiment of the present invention, in the inspecting method, the flexible display device is only attached with an electrode layer of an electrode structure, and during the performance inspection, a required inspecting electric field is supplied to the flexible display device by the electrode layer and a corresponding external electrode.

According to an embodiment of the present invention, in the inspecting method, the flexible display device has already a pair of electrode structures, and during the performance inspection, a required inspecting electric field is supplied to the flexible display device by the electrode structures.

The present invention provides a system for inspecting a flexible device, which is used for performing a performance inspection on a flexible device when the flexible device is in a bending state, or after the flexible device has finished bending test so as to obtain a mechanical reliability. The inspecting system includes at least one bending unit with at least one curvature, a conveyor unit used for conveying the flexible device so that a portion of the flexible device is passing through the bending unit and is bent into a bending portion, and an inspecting unit used for performing a performance inspection on the flexible device.

According to an embodiment of the present invention, in the inspecting system, the inspecting unit performs the performance inspection on at least one point of the bending portion.

According to an embodiment of the present invention, in the inspecting system, the inspecting unit performs the performance inspection on the flexible device after the flexible device has finished bending test, so as to obtain a mechanical reliability of the flexible device.

According to an embodiment of the present invention, in the inspecting system, the performance inspection includes electrical, optical, or opto-electric inspection, and an inspection result can be recorded, displayed or both.

According to an embodiment of the present invention, in the inspecting system, the flexible device can be a flexible display device without an attached electrode structure, and the inspecting unit supplies a required inspecting electric field to the flexible display device from external.

According to an embodiment of the present invention, in the inspecting system, the flexible display device is only attached with an electrode layer of an electrode structure, wherein the inspecting unit supplies a required electric field to the flexible display device through the electrode layer and an external electrode. Alternatively, the flexible display device has a pair of electrodes, which can be used to provide the required electric field.

The invention described here makes possible the advantages of (1) providing a system to associate the conveyer in the roll to roll process with the inspection system to simplify the manufacture and inspection system of the flexible device, and (2) providing a method to realize such a system.

In order to make the aforementioned and other objects, features and advantages of the present invention comprehensible, a preferred embodiment accompanied with figures is described in detail below.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

A flexible device can be bent due to its flexibility. For example, a flexible display can be used in a bending state directly or stored in curved shape. However, the display performance of the flexible display may be affected when it is bent. In addition, the flexible display may be damaged due to bending. Therefore, inspections of bent flexible devices and flexible devices finished bending test need to be proceeded, and the latter one is also referred to as mechanical reliability inspection.

Figure 1A:
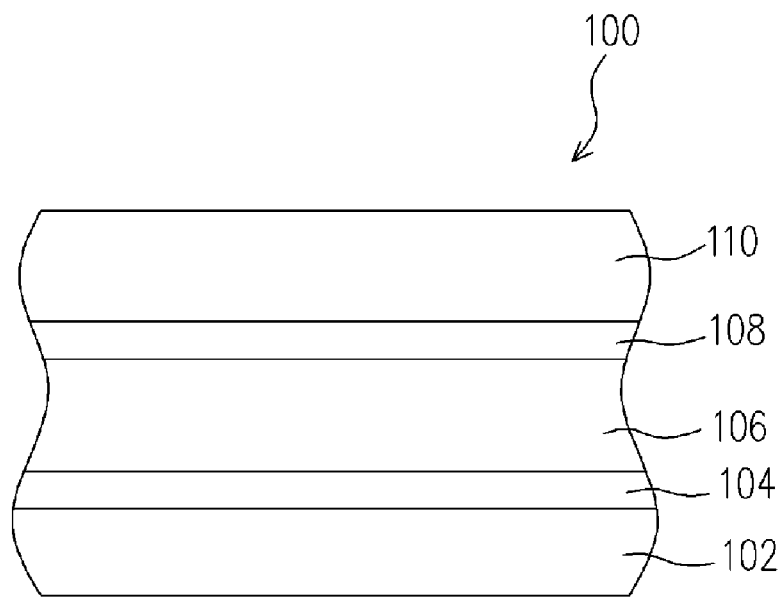
FIGS. 1A to 1B are diagrams illustrating the basic structure of a flexible display to be inspected according to an embodiment of the present invention.
Figure 1B:
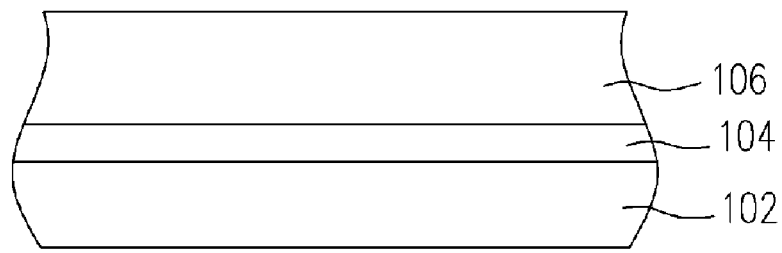

FIGS. 1A to 1B are diagrams illustrating the basic structure of a flexible display to be inspected according to an embodiment of the present invention. Wherein, the flexible device is described as a flexible display as example. Referring to FIG. 1A, the basic structure of the flexible display 100 includes: a flexible display medium layer 106. One or two adhesive layers 104 and 108 is disposed on one or both of the upper and lower surfaces of the flexible display medium layer 106. In addition, a driving electrode structure includes an upper electrode layer 110 and a lower electrode layer 102, which are adhered to one or both of the upper and lower surfaces of the flexible display medium layer 106 through the adhesive layers 108 and 104 respectively. As to FIG. 1B, only an electrode layer 102 is completed and the upper electrode layer 110 is not completed yet. In addition, the flexible display medium layer 106 with neither electrode layer can also be inspected alone. In other words, according to the present invention, a flexible display device 100 with complete or incomplete electrode structure can be inspected. In addition, the incomplete electrode structure refers to, e.g. having a single electrode layer 102 or having no electrode layer. Other actual structures of the flexible display described above are well-known to those skilled in the ordinary art, so will not be described again.

Figure 2:
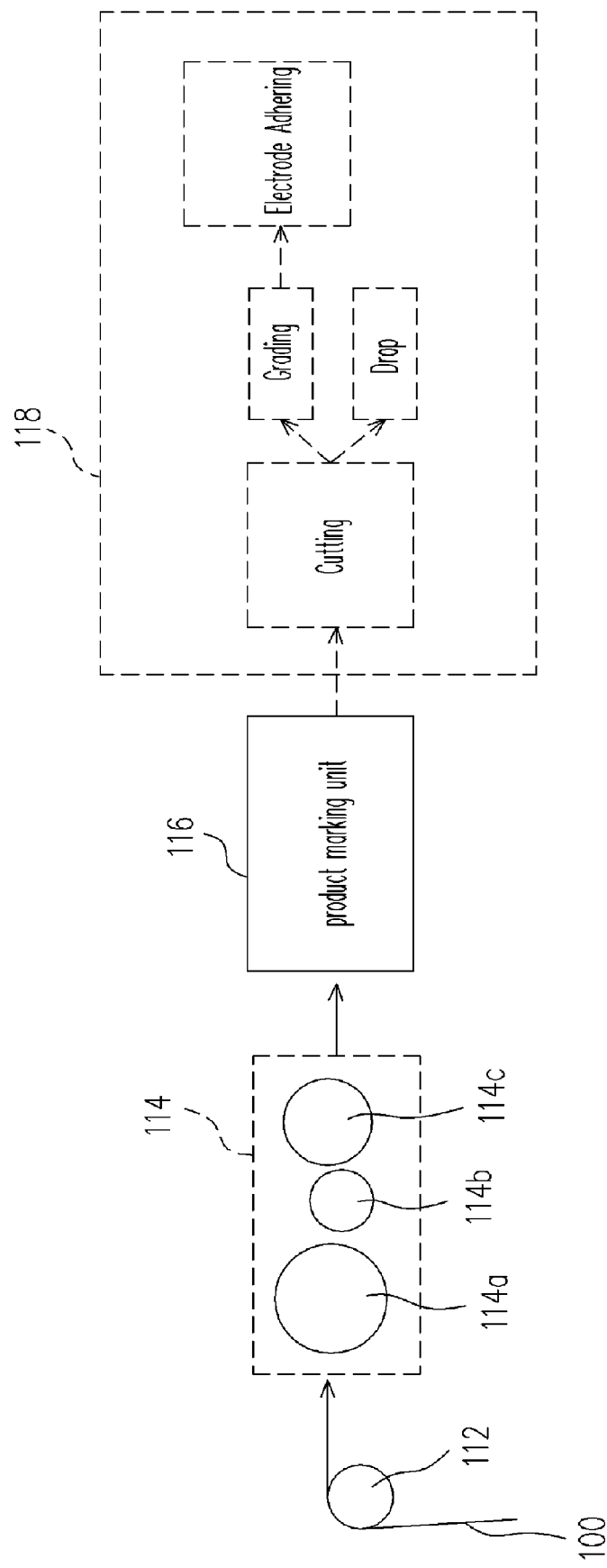
FIG. 2 is an inspecting flowchart on a flexible display device according to an embodiment of the present invention.

FIG. 2 is an inspecting flowchart on a flexible display device according to an embodiment of the present invention. Referring to FIG. 2, the flexible display device 100 is conveyed by a conveyor unit 112 to be passing through a bending unit 114. In the bending unit 114, the flexible display device 100 is bent with at least one curvature. FIG. 2 illustrates rollers 114a to 114c with different curvatures as examples. However, there can be one or multiple rollers in the actual design, and the radiuses or curvatures can be the same or different. These can all be alternatively chosen based on the actual design. In addition, the manner illustrated in FIG. 2 is only an embodiment, wherein the conveyor unit 112 conveys the flexible display device 100 by external driving to pass the flexible display device 100 through the bending unit 114. However, the conveyor unit 112 can also be integrated with the bending unit 114. That means the rollers 114a to 114c on the bending unit 114 can provide convey function at the same time.

In addition, if the performance of the flexible display device in bending state is to be inspected, the bending unit 114 can be integrated with an inspecting unit (not shown in FIG. 2) to perform a performance inspection, e.g. electrical, optical, or opto-electric inspection, on the bending portion at the same time, and an inspection result can be recorded, displayed or both.

And if a mechanical reliability inspection is to be performed, the flexible display device is bent first before performing a performance inspection to ensure that the flexible display device is not damaged after being bent.

In addition, if it is necessary, the inspected product can be directly marked after inspection. Moreover, in the subsequent process 118, the steps of, e.g. cutting, grading, drop, electrode adhering etc. are included. These detailed flows can be changed according to the actual arrangement, so won't be described here.

Figure 3:
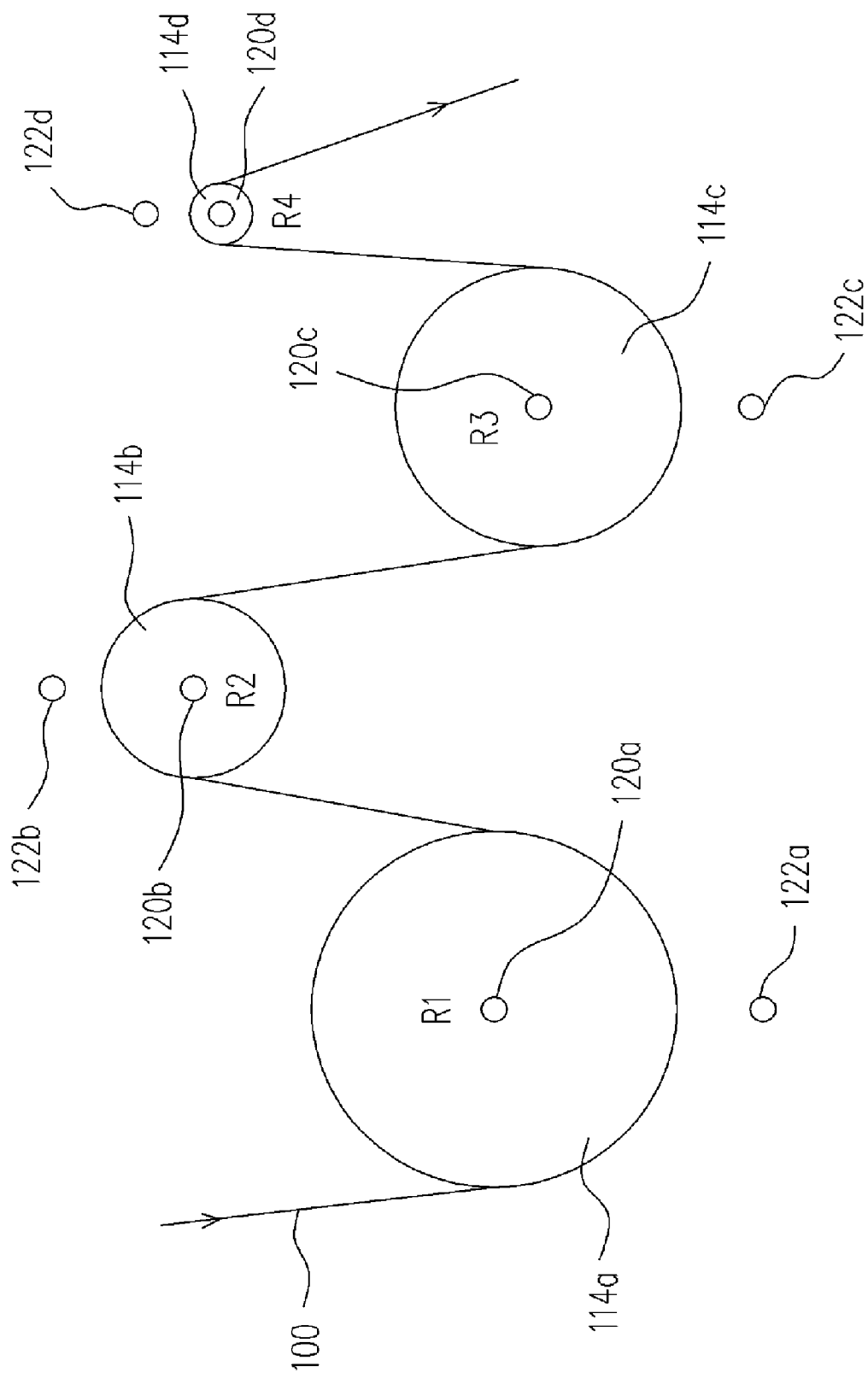
FIG. 3 is a schematic block diagram illustrating the integration of a bending unit and an inspecting unit according to an embodiment of the present invention.

The integrated structure of the bending unit 114 and an inspecting unit, as shown in FIG. 3, is described below. Referring to FIG. 3, when the inspected flexible display device 100 is passing through the bending unit 114, it will be bent with at least one predetermined curvature, e.g. four different curvatures. The method to produce curvatures is, e.g. to use rollers 114a to 114d of different radiuses along with the conveying of the inspected flexible display device 100. The radiuses of the rollers 114a to 114d are, e.g. R1, R2, R3, and R4, which may be the same or different based on the actual design.

As to the inspecting components, e.g. the roller 114a, a light source 120a can be disposed inside the roller 114a. In addition, a detector 122a can be disposed at the external of the roller 114a to receive light signals passing through the flexible display device 100. In the present embodiment, it is assumed that the flexible display device 100 is transmissive. If the flexible display device 100 is reflective, then the light source 120a and the detector 122a can be at the same side, and the detector 122a receives light signals reflected by the flexible display device 100. Moreover, the position disposition of the light source 120a and the detector 122a in FIG. 3 is only an embodiment and is not the only option. For example, the positions of the light source 120a and the detector 122a can be switched, or can be more variations as described below.

If only the optical features are to be inspected on the flexible display device 100, there is no need to supply an electric field. If the electrical or opto-electric features are to be inspected, an electric field needs to be supplied to the flexible display medium layer 106 (refer to FIG. 1A) of the flexible display device 100. Here, if the flexible display device 100 is with complete electrode structure, the required electric field can be supplied by the electrode structure. And if the flexible display device 100 has no incomplete electrode structures, the electric field has to be supplied from external through external electrode structures. Furthermore, if a single electrode layer (refer to FIG. 1B) has been completed on the flexible display device 100, the required electric field can be supplied by an external electrode along with the electrode layer.

Figure 4A:
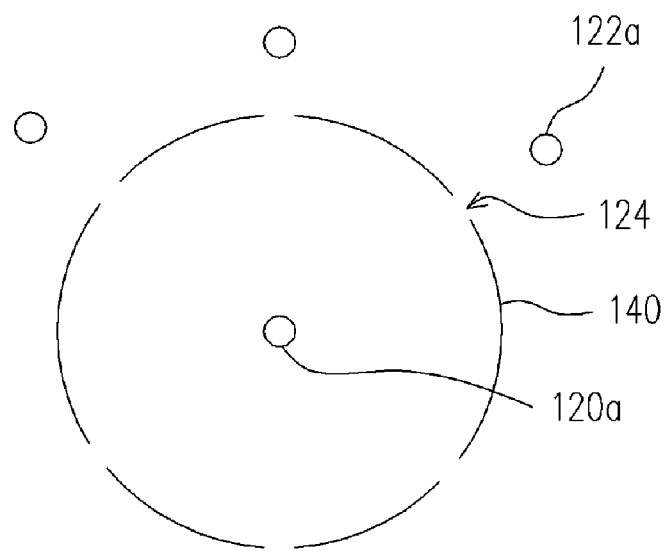
FIGS. 4A to 4B are schematic block diagrams of a roller according to an embodiment of the present invention.
Figure 4B:
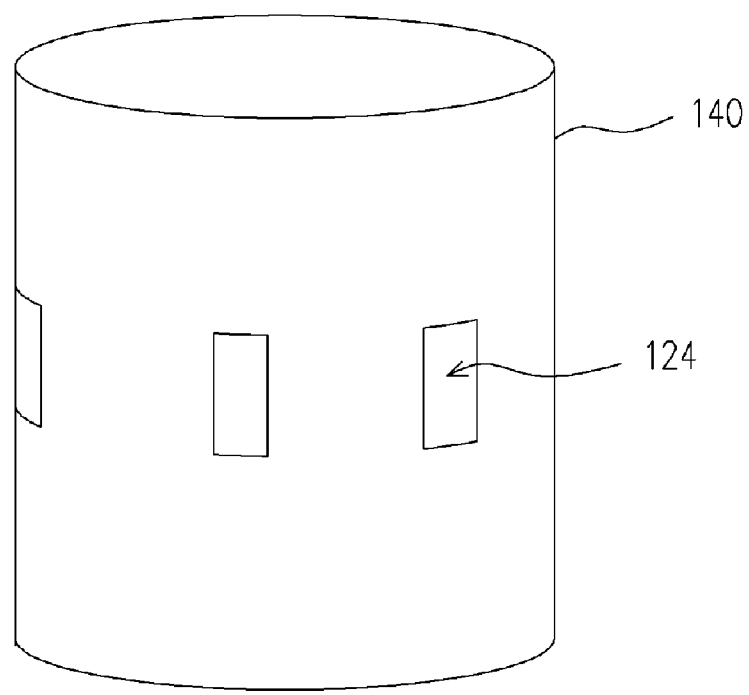

Generally, the material of the rollers 114a to 114d can be light transmissive material. And the design in FIGS. 4A to 4B can be adopted if the material of the rollers 114a to 114d is not light transmissive. FIG. 4A is a cross-sectional view illustrating the structure of a roller according to an embodiment of the present invention. FIG. 4B is a perspective view illustrating the structure of a roller according to an embodiment of the present invention. Referring to FIGS. 4A and 4B, one or a plurality of transmissive regions 124, which can also be an opening structure, is arranged on the surface of the roller 140. The opening structure can be the regional openings, or can be long openings extending along the longitudinal direction of the roller 140. And a detector 122a, which can detect a plurality of regions simultaneously, can be disposed along with a plurality of transmissive regions 124, and the openings are not necessarily distributed on the same cross section circle, instead, they can be distributed in dot array.

Figure 5:
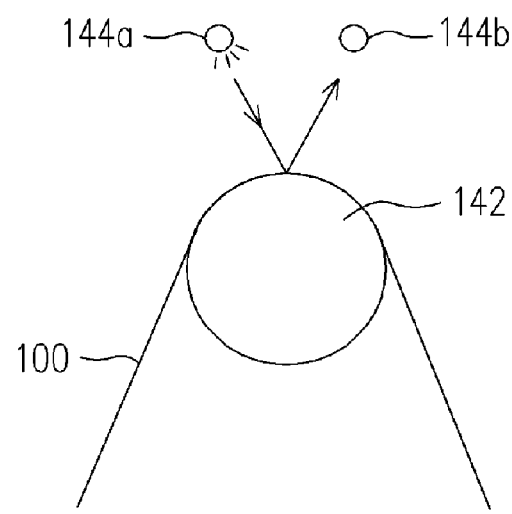
FIG. 5 is another schematic block diagram according to an embodiment of the present invention.

FIG. 5 is another schematic block diagram according to an embodiment of the present invention. Referring to FIG. 5, if the flexible display device is reflective, then the light source 144a and the detector 144b can be both disposed at the external of the roller 142. The light emitted from the light source irradiates at the region to be inspected and is reflected. The detector receives the reflected light signals.

Figure 6:
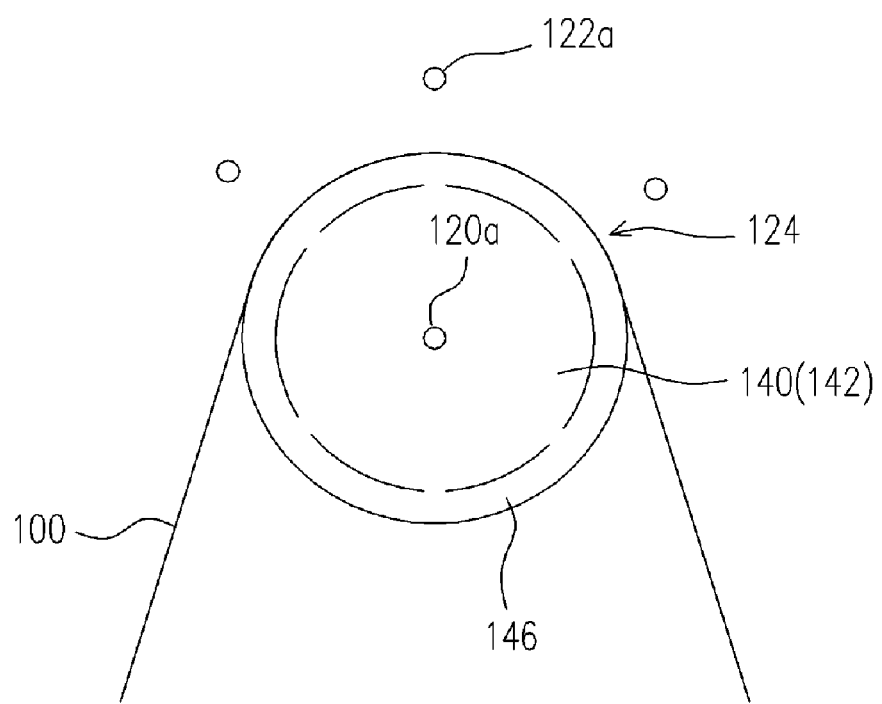
FIG. 6 is a diagram illustrating one of the structures of supplying electric filed from external according to an embodiment of the present invention.

Regarding the design of the externally supplied electric field, FIG. 6 is a drawing, schematically illustrating one of the structures of supplying electric filed from external according to an embodiment of the present invention. Referring to FIG. 6, if the flexible display device 100 has already a complete single electrode layer, an electrode layer 146 can be disposed on the surface of the roller 140. The electrode layer 146 is used along with the single electrode layer of the flexible display device 100 to produce the electric field. Accordingly, the performance inspection can be performed in a bending state.

Figure 7:
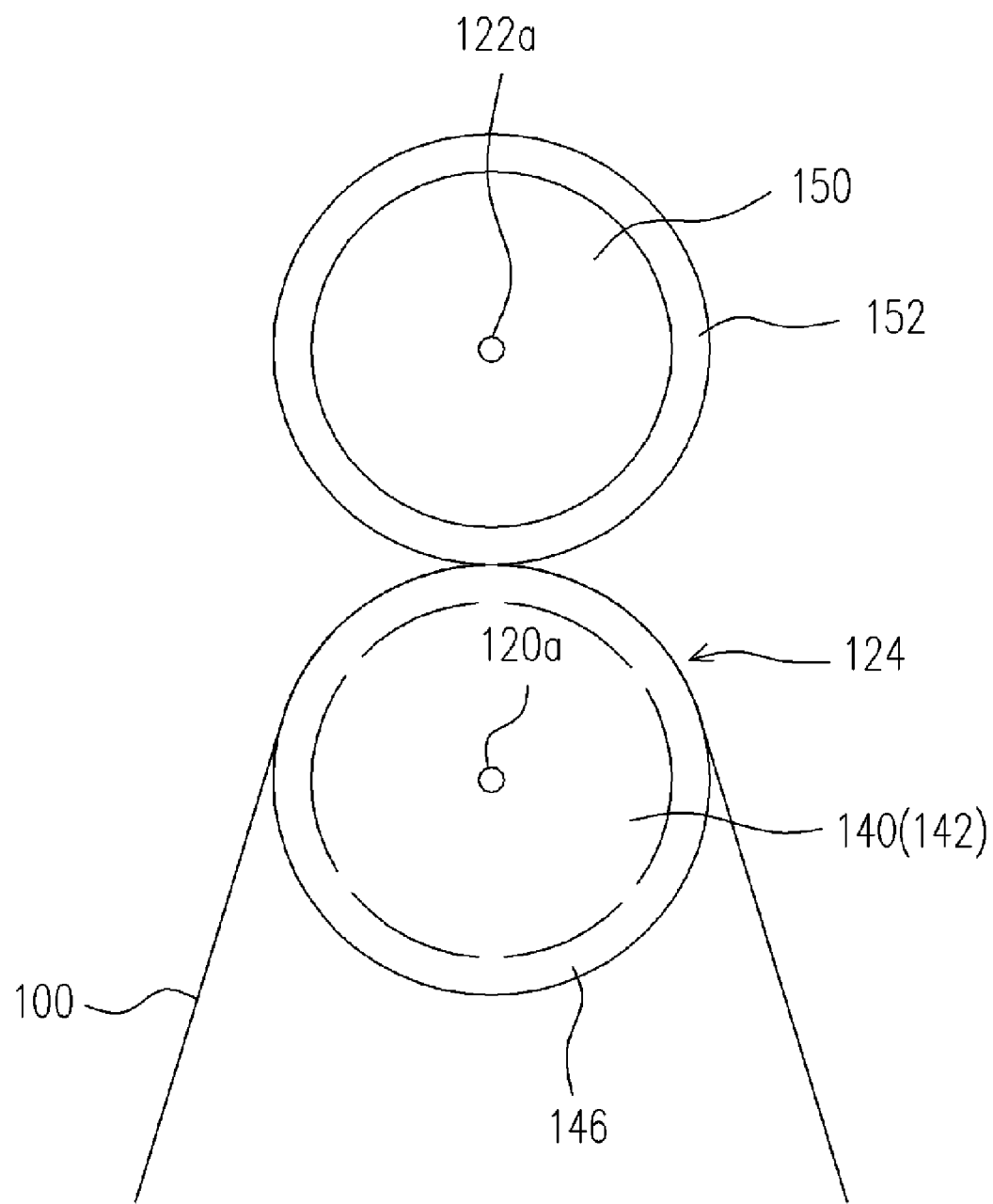
FIG. 7 is a diagram illustrating another one of the structures of supplying electric filed from external according to an embodiment of the present invention.

FIG. 7 is a diagram illustrating another one of the structures of supplying electric filed from external according to an embodiment of the present invention. Referring to FIG. 7, if the flexible display device 100 is not disposed with electrode layer, for example, only the flexible display medium layer 106 in FIG. 1A, then an electrode layer 146 can be disposed on the surface of the roller 140, as shown in FIG. 6. And another electrode can be achieved by, for example, another roller electrode. That is, an electrode layer 152 is also disposed on the surface of the roller 150.

Accordingly, the electrode layer 146 is used along with the electrode layer 152 to produce the electric field. Moreover, with the disposition of the roller 150, the detector 122a can also be disposed inside the roller 150. And the design of the roller 150 can also be changed into a flat panel electrode (not shown), and the electric field is supplied to the flexible display medium layer 106 by the flat panel electrode and the electrode layer 146 on the surface of the roller.

It is noticeable that generally an external electric field needs to be produced only if the flexible display device 100 has incomplete electrode layer. The embodiments described above are embodiments with externally produced electric field, but the present invention is not limited to the arrangements of these embodiments. The arrangements of the light source and the detector also can be altered based on to the actual arrangement.

In addition, during the inspection process, the inspecting system of the present invention may also include a record unit which can record, display, or both. The record unit is coupled to the detector to be integrated into a part of the inspecting unit. For example, the inspection result can be stored into the memory of a computer system, and can be displayed in the display of a computer system too. The result information recorded by the record unit can be used in, for example, the subsequent steps 116 and 118 in FIG. 2.

The mechanical reliability inspection is to inspect whether the flexible display device is damaged after it has been bent. Thus, the performance inspection does not have to be performed while the device is bent. The performance inspection can also be performed when the flexible display device is flat and expanded. If the required inspection electric field needs to be produced with an external electrode, a simpler flat panel electrode method can be used to supply the electric field to the flexible display medium layer 106 in the flexible display device besides using and altering some mechanisms described above.

The present invention is not limited to the embodiments described above. A required actual design can be obtained by combining and altering all the features of all aforementioned embodiments appropriately. In particular, for example, the structure design of the externally supplied electric field, some of the features of the aforementioned embodiments can be adopted besides those specific descriptions of the embodiments. In other words, the embodiments described above can be integrated or separated appropriately as long as the performance inspection or the mechanical reliability inspection can be performed when the flexible display device is in a bending state.

In overview, according to the present invention, a bending unit can perform a performance inspection on a flexible display device by combining the operation of an inspecting unit when the flexible display device is being bent. Also and, after the flexible display device has been ever bent, a performance inspection is performed to ensure the mechanical reliability of the flexible display device. Accordingly, the bendable flexible displays can be well inspected to improve the reliability of the products.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method for inspecting flexible display device, comprising:

providing a flexible display device to be inspected, wherein the flexible display device comprises at least one functional layer to be inspected;

providing at least one bending unit with at least one curvature;

conveying the flexible display device, to pass a portion of the flexible display device over a surface of the bending unit so that the portion of the flexible display device is bent into a bending portion; and performing a performance inspection on the flexible display device.

2. The inspection method as claimed in claim 1, wherein the performance inspection includes electrical, optical, or opto-electric inspection.

3. The inspection method as claimed in claim 1, wherein the flexible display device, and the steps of the performance inspection include:

supplying a required electric field to the flexible display device from external; and performing an opto-electric or optical inspection on the flexible display device without an electrode structure attached.

4. The inspection method as claimed in claim 1, wherein the flexible display device having an electrode layer of an electrode structure, and during the performance inspection, a required inspecting electric field is supplied to the flexible display device by the electrode layer and an external electrode.

5. The inspection method as claimed in claim 1, wherein the flexible display device having a pair of electrode structures, and during the performance inspection, a required electric field is supplied to the flexible display device by using the electrode structures.

6. A system for inspecting flexible display device, comprising:

at least one bending unit with at least one curvature;

a conveyor unit, used for conveying a flexible display device so that a portion of the flexible display device is passing through the bending unit and is bent into a bending portion; and an inspecting unit, used for performing a performance inspection on the flexible display device.

7. The inspection system as claimed in claim 6, wherein the performance inspection includes electrical, optical, or opto-electric inspection.

8. The inspection system as claimed in claim 6, wherein the at least one bending unit includes one bending unit or multiple bending units with the same curvature or different curvatures.

9. A method for inspecting flexible display device, comprising:

providing a flexible display device to be inspected;

conveying the flexible display device, so that a portion of the flexible display device is bent into a bending portion; and performing a performance inspection on the flexible display device.

10. The inspection method as claimed in claim 9, wherein the performance inspection is performed on at least one point of the bending portion about at least one of electrical property, optical property, or opto-electric property.

11. The inspection method as claimed in claim 9, wherein the performance inspection is performed on the flexible display device at a non-bending state after the flexible display device has finished bending test, so as to obtain a mechanical reliability of the flexible display device.

12. The inspection system as claimed in claim 6, wherein the flexible display device without an electrode structure attached, and the inspecting unit supplies a required inspecting electric field to the flexible display device from external to perform an opto-electric or optical inspection.

13. The inspection system as claimed in claim 6, wherein the flexible display device having an electrode layer of an electrode structure, and the inspecting unit supplies a required inspecting electric field to the flexible display device using the electrode layer and a corresponding external electrode.

14. The inspection system as claimed in claim 6, wherein the flexible display device with an electrode structure attached, and the electrode structure is used for supplying a required inspecting electric field to the flexible display device.

* * * * *